(12) United States Patent
Pecherer

(10) Patent No.: US 8,251,898 B2
(45) Date of Patent: Aug. 28, 2012

(54) LARYNGOSCOPE APPARATUS WITH ENHANCED VIEWING CAPABILITY

(75) Inventor: Eugeny Pecherer, Netanya (IL)

(73) Assignee: Truphatek International Ltd, Netanya (IL)

( * ) Notice: Subject to any disclaimer, the term of this patent is extended or adjusted under 35 U.S.C. 154(b) by 275 days.

(21) Appl. No.: 12/672,399

(22) PCT Filed: Aug. 7, 2008

(86) PCT No.: PCT/IL2008/001093
§ 371 (c)(1),
(2), (4) Date: Feb. 5, 2010

(87) PCT Pub. No.: WO2009/019703
PCT Pub. Date: Feb. 12, 2009

(65) Prior Publication Data
US 2011/0060190 A1    Mar. 10, 2011

(30) Foreign Application Priority Data
Aug. 7, 2007 (IL) .......................................... 185112

(51) Int. Cl.
*A61B 1/267* (2006.01)
(52) U.S. Cl. ........................................................ 600/188
(58) Field of Classification Search ........... 600/185–200
See application file for complete search history.

(56) References Cited

U.S. PATENT DOCUMENTS

| | | | |
|---|---|---|---|
| 330,139 A | 11/1885 | Meyer | |
| 2,433,705 A | 12/1947 | Palmeter | |
| 3,426,749 A | 2/1969 | Jephcott | |
| 3,598,113 A | 8/1971 | Moore et al. | |
| 3,638,644 A | 2/1972 | Reick | |
| 3,766,909 A | 10/1973 | Ozbey | |
| 3,826,248 A | 7/1974 | Gobels | |
| 3,856,001 A | 12/1974 | Phillips | |
| 3,874,371 A | 4/1975 | Stader et al. | |
| 4,037,588 A | 7/1977 | Heckele | |
| 4,086,919 A | 5/1978 | Bullard | |
| 4,273,112 A | 6/1981 | Heine et al. | |
| 4,306,547 A | 12/1981 | Lowell | |
| 4,406,280 A | 9/1983 | Upsher | |
| 4,437,458 A | 3/1984 | Upsher | |
| 4,527,553 A | 7/1985 | Upsher | |
| 4,556,052 A | 12/1985 | Muller | |
| 4,557,256 A | 12/1985 | Bauman | |
| 4,565,187 A | 1/1986 | Soloway | |

(Continued)

FOREIGN PATENT DOCUMENTS

DE    26 21 232    11/1977

(Continued)

OTHER PUBLICATIONS

International Search Report mailed on Nov. 13, 2008 in International Publication No. WO 2009/019703 A2, published Feb. 12, 2009.

(Continued)

*Primary Examiner* — Ellen C Hammond
(74) *Attorney, Agent, or Firm* — Abraham Hershkovitz; Harold L. Novick; Hershkovitz & Associates, LLC

(57) ABSTRACT

Laryngoscope apparatus including a curved laryngoscope blade and an optical system for affording a field of view along a deflected line of sight for reducing patient manipulation and/or the degree of force required to achieve a good glottic view.

16 Claims, 7 Drawing Sheets

A=25mm
B=32mm
DISTORTION A/B=0.78

U.S. PATENT DOCUMENTS

| | | |
|---|---|---|
| 4,570,614 A | 2/1986 | Bauman |
| 4,579,108 A | 4/1986 | Bauman |
| 4,583,527 A | 4/1986 | Musicant et al. |
| 4,596,239 A | 6/1986 | Bauman |
| 4,679,547 A | 7/1987 | Bauman |
| 4,878,486 A | 11/1989 | Slater |
| 4,884,558 A | 12/1989 | Gorski et al. |
| 4,901,708 A | 2/1990 | Lee |
| 4,924,855 A | 5/1990 | Salerno et al. |
| 4,930,495 A | 6/1990 | Upsher |
| 4,958,624 A | 9/1990 | Stone et al. |
| 4,972,825 A | 11/1990 | Vescovo, Jr. |
| 5,060,633 A | 10/1991 | Gibson |
| 5,065,738 A | 11/1991 | Van Dam |
| 5,178,131 A | 1/1993 | Upsher |
| 5,263,472 A | 11/1993 | Ough |
| 5,355,870 A | 10/1994 | Lacy |
| 5,363,838 A | 11/1994 | George |
| 5,501,651 A | 3/1996 | Bauman |
| 5,529,570 A | 6/1996 | Storz |
| 5,643,221 A | 7/1997 | Bullard |
| 5,651,760 A | 7/1997 | Upsher |
| 5,702,351 A | 12/1997 | Bar-Or et al. |
| 5,776,053 A | 7/1998 | Dragisic et al. |
| 5,827,178 A | 10/1998 | Berall |
| 5,842,973 A | 12/1998 | Bullard |
| 5,873,818 A | 2/1999 | Rothfels |
| 5,879,304 A | 3/1999 | Shuchman et al. |
| 5,951,461 A | 9/1999 | Nyo et al. |
| 5,973,728 A | 10/1999 | Levitan |
| 6,013,026 A | 1/2000 | Krauter et al. |
| 6,036,639 A | 3/2000 | Allred, III et al. |
| 6,123,666 A | 9/2000 | Wrenn et al. |
| 6,139,491 A | 10/2000 | Heine et al. |
| 6,213,937 B1 | 4/2001 | Vivenzio |
| 6,350,235 B1 | 2/2002 | Cohen et al. |
| 6,354,993 B1 | 3/2002 | Kaplan et al. |
| RE37,861 E | 9/2002 | Schneider |
| 6,444,358 B1 | 9/2002 | Allred, III et al. |
| 6,508,759 B1 | 1/2003 | Taylor et al. |
| 6,652,453 B2 | 11/2003 | Smith et al. |
| 6,655,377 B2 | 12/2003 | Pacey |
| 6,676,598 B2 | 1/2004 | Rudischhauser et al. |
| 6,719,688 B2 | 4/2004 | Pecherer et al. |
| 6,840,903 B2 | 1/2005 | Mazzei et al. |
| 6,964,637 B2 | 11/2005 | Dalle et al. |
| 7,044,910 B2 | 5/2006 | Cartledge et al. |
| 7,128,710 B1 | 10/2006 | Cranton et al. |
| 7,214,184 B2 | 5/2007 | McMorrow |
| 7,338,440 B1 | 3/2008 | Smith |
| 7,500,948 B2 | 3/2009 | Cantrell |
| 7,608,040 B1 | 10/2009 | Dunst |
| 7,736,304 B2 | 6/2010 | Pecherer |
| 7,771,350 B2 | 8/2010 | Geist et al. |
| 7,802,909 B2 | 9/2010 | Baker |
| 7,909,759 B2 | 3/2011 | Pecherer |
| 7,946,981 B1 | 5/2011 | Cubb |
| 2002/0082477 A1 | 6/2002 | Kim |
| 2002/0082478 A1 | 6/2002 | McGrath |
| 2003/0092967 A1 | 5/2003 | Fourie et al. |
| 2003/0195390 A1 | 10/2003 | Graumann |
| 2004/0034281 A1 | 2/2004 | Cartledge et al. |
| 2004/0122292 A1 | 6/2004 | Dey et al. |
| 2004/0127770 A1 | 7/2004 | McGrath |
| 2004/0215062 A1 | 10/2004 | Dalle et al. |
| 2005/0090712 A1 | 4/2005 | Cubb |
| 2007/0093693 A1 | 4/2007 | Geist et al. |
| 2007/0167686 A1 | 7/2007 | McGrath |
| 2008/0004498 A1 | 1/2008 | Pecherer |
| 2009/0065007 A1 | 3/2009 | Wilkinson et al. |
| 2009/0209816 A1 | 8/2009 | Gunther Nielsen et al. |
| 2009/1029914 | 12/2009 | McGrath |
| 2010/0261968 A1 | 10/2010 | Nearman et al. |

FOREIGN PATENT DOCUMENTS

| | | |
|---|---|---|
| DE | 85 26 662 | 10/1985 |
| DE | 202 18 560 | 5/2003 |
| EP | 0 184 588 | 6/1986 |
| GB | 685741 | 1/1953 |
| GB | 806467 | 12/1958 |
| GB | 2437435 | 10/2007 |
| WO | WO 2004/096032 | 11/2004 |
| WO | WO 2006/056976 | 6/2006 |
| WO | WO 2006/131770 | 12/2006 |
| WO | WO 2007/066134 | 6/2007 |

OTHER PUBLICATIONS

Medizintechnik KaWe Germany, Laryngoskope, Megalight F.O. (Publication date unknown).

Hilbro brochure, "Green system fiber optic laryngoscope (Interchangeable light guide insert)," 2001.

Rüsch Inc. "Care and Maintenance instructions for Rüsch Laryngoscope Handles and Blades," 2001.

Machine translation of DE 26 21 232.

Machine translation of DE 85 26 662.

Machine translation of DE 202 18 560.

A=23mm
B=29mm
DISTORTION A/B=0.79

A=25mm
B=32mm
DISTORTION A/B=0.78

| SURFACES | SCHOTT BK7 |
|---|---|
| ROC (mm) S1 | 77.52 ±0.2 |
| ROC (mm) S2 | ∞ |
| INDEX OF REFRACTION | 1.517 @ 0.588μ |

| SURFACES | S1 | S2 |
|---|---|---|
| SURFACE SHAPE | CONVEX | PLANO |
| CLEAR APERTURE | ϕ8.5 | ϕ8.5 |
| SURFACE FIGURE (POWER) | 2λ @ 0.633μ | 2λ @ 0.633μ |
| SURFACE IRREGULARITIES | λ @ 0.633μ | λ @ 0.633μ |
| SURFACE QUALITY (MIL 0-13830A) | 60/40 | 60/40 |
| ETV | <15μ | |

| MATERIAL: SCHOTT 8K7 OR EQUIVALENT |
|---|
| INDEX OF REFRACTION: 1.517 @ 0.588μ |
| DIAMETER: 9.0 −0.05mm |
| THICKNESS: SEE DRAWING |

| SURFACES | S1 | S2 |
|---|---|---|
| ROC (mm) | 22.06 ±0.1 | 180.0 ±3.0 |
| SURFACE SHAPE | CONCAVE | CONCAVE |
| CLEAR APERTURE | φ8.5 | φ8.5 |
| SURFACE FIGURE (POWER) | 2λ @ 0.633μ | 2λ @ 0.633μ |
| SURFACE IRREGULARITIES | λ @ 0.633μ | λ @ 0.633μ |
| SURFACE QUALITY (MIL 0-13830A) | 60/40 | 60/40 |
| PRISM ANGLE α | | 55°±0.5° |

LARYNGOSCOPE APPARATUS WITH ENHANCED VIEWING CAPABILITY

FIELD OF THE INVENTION

CROSS-REFERENCE TO RELATED APPLICATIONS

This application is the U.S. national phase application of PCT application Ser. No. PCT/IL2008/001093 having an international filing date of 7 Aug. 2008.

The invention pertains to a laryngoscope apparatus with enhanced viewing capability.

BACKGROUND OF THE INVENTION

Physicians performing an intubation procedure with a conventional laryngoscope assume an appropriate position behind a patient's head and manipulate his head to maximize visualization of his laryngeal area for enabling Endotracheal Tube (ETT) placement. In certain instances, a patient's head cannot be moved which can considerably complicate an intubation. Physicians can use a laryngoscope blade to apply force to a patient's internal surfaces to assist visualization of his larynx to enable intubation. Applying a greater force typically improves a physician's visualization of a patient's larynx but traumatizes surrounding tissues. Most patients suffer at least some trauma during conventional intubation procedures.

U.S. Pat. No. 5,873,818 to Rothfels, the contents of which are incorporated herein by reference, illustrates and describes an optical system (44) for use with a curved laryngoscope blade (16) with a leading blade tip (46) for optically assisting visualization of a patient's laryngeal region thereby reducing the need for manipulation of a patient's head and/or application of force for sighted intubations. The optical system (44) includes a plano-convex eyepiece lens (48) and a prism lens (50) having a prism optic (54) with a smooth or flat sloping prism surface (not denoted by a reference number) and a further lens (56) with a concave surface (also not denoted by a reference number) facing the eyepiece lens (48). The concave surface of the further lens (56) serves to provide a wide angle view while the companion prism optic (54) directs the view toward the blade tip (46) to better expose the larynx. Also, the further lens (56) "miniaturizes" objects view while the eyepiece lens (48) compensates for the miniaturization as well as for providing focusing (see U.S. Pat. No. '818 Col. 3, lines 21 to 25). The prism optic (54) and the further lens (56) can be assembled together or optionally molded in one piece. Laryngoscope blades can be integrally formed with an optical system or alternatively be configured to removably receive a discrete optical view tube housing an optical system (see U.S. Pat. No. '818 Col. 2, line 67 to Col. 3, line 3).

SUMMARY OF THE PRESENT INVENTION

The present invention is for a laryngoscope apparatus for optically assisting a good glottic view thereby minimizing the need for manipulation of a patient's head and/or application of force. The present invention is based on the realization that an increased Field Of View (FOV) magnification compared to a FOV magnification achievable in a Rothfels arrangement serves to provide a Line Of Sight (LOS) with a most deflected LOS ray which is more deflected than its counterpart most deflected LOS ray in the Rothfels arrangement. This increased FOV magnification for an identical Rothfels arrangement typically having a rearmost concave surface serving a maximum possible FOV is enabled by replacing Rothfels' forwardmost flat inclined prism surface by a forwardmost concave inclined prism surface.

It should be noted that the inclination of the proposed forwardmost concave inclined prism surface limits its radius of curvature to a far greater radius of curvature compared to the radius of curvature at its opposite rearmost concave surface facing the eyepiece lens and therefore affords a relatively small additional FOV magnification but its contribution to the LOS deflection is surprisingly significant in minimizing the need for manipulation of a patient's head and/or the application of force for a good glottic view. Moreover, the forwardmost concave inclined prism surface introduces additional FOV distortion and also is more difficult to manufacture than the hitherto forwardmost flat inclined prism surface but these disadvantages are more than compensated by the advantageous clinical considerations.

Laryngoscope apparatus in accordance with the present invention can be implemented as a laryngoscope blade with either an integral optical system or intended for use with a discrete optical view tube. Such laryngoscope blades preferably include an illumination arrangement for providing illumination light for assisting intubation and a defogging arrangement for defogging their forwardmost concave inclined prism surface. Such laryngoscope blades are permanently mounted on a laryngoscope handle and pivotal between an inoperative storage position and an operative intubation position in a penknife-like manner or detachably mounted on a laryngoscope handle. Exemplary handheld penknife-like laryngoscopes are illustrated and described in commonly owned PCT International Application No. PCT/IL2005/001232 entitled Handheld Penknife-Like Laryngoscope published under PCT International Publication No. WO 2006/056976 on Jun. 1, 2006, the contents of which are incorporated herein by reference. Detachable laryngoscope blades can be of either the ISO 7376/1 type including a light source for detachable mounting on a laryngoscope handle having a power pack only or the ISO 7376/3 type including a light pipe for detachable mounting on a laryngoscope handle including both a power pack and a light source.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1A:
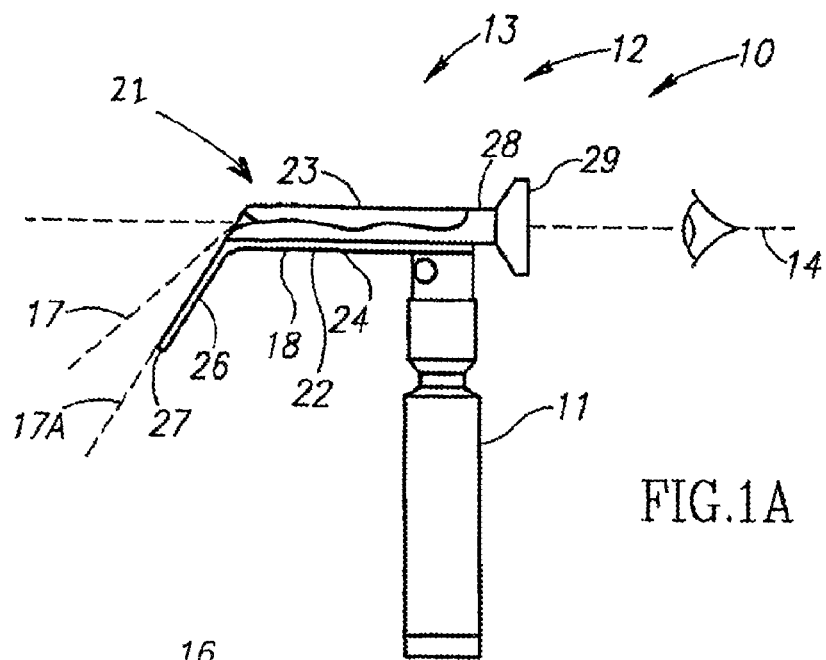
FIG. 1A is a pictorial representation showing a laryngoscope including laryngoscope apparatus for affording a magnified Field Of View (FOV) along a deflected line of sight in a median plane through the midline of a human body for assisting an intubation procedure.
Figure 1B:
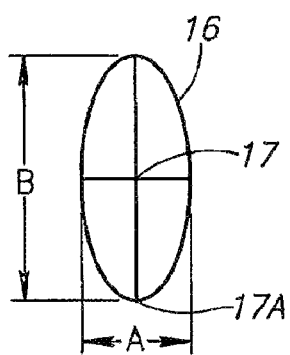
FIG. 1B is a pictorial representation of FIG. 1A's FOV having a minor axis A and a major axis B in the median plane.
Figure 1C:
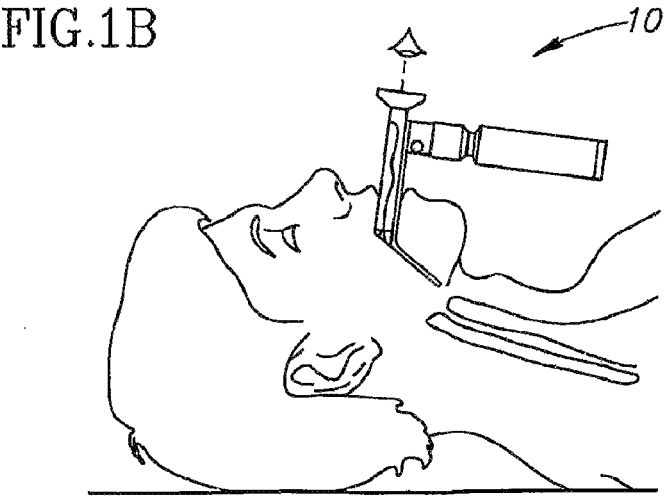
FIG. 1C is a pictorial representation showing the use of FIG. 1A's laryngoscope.
Figure 2:
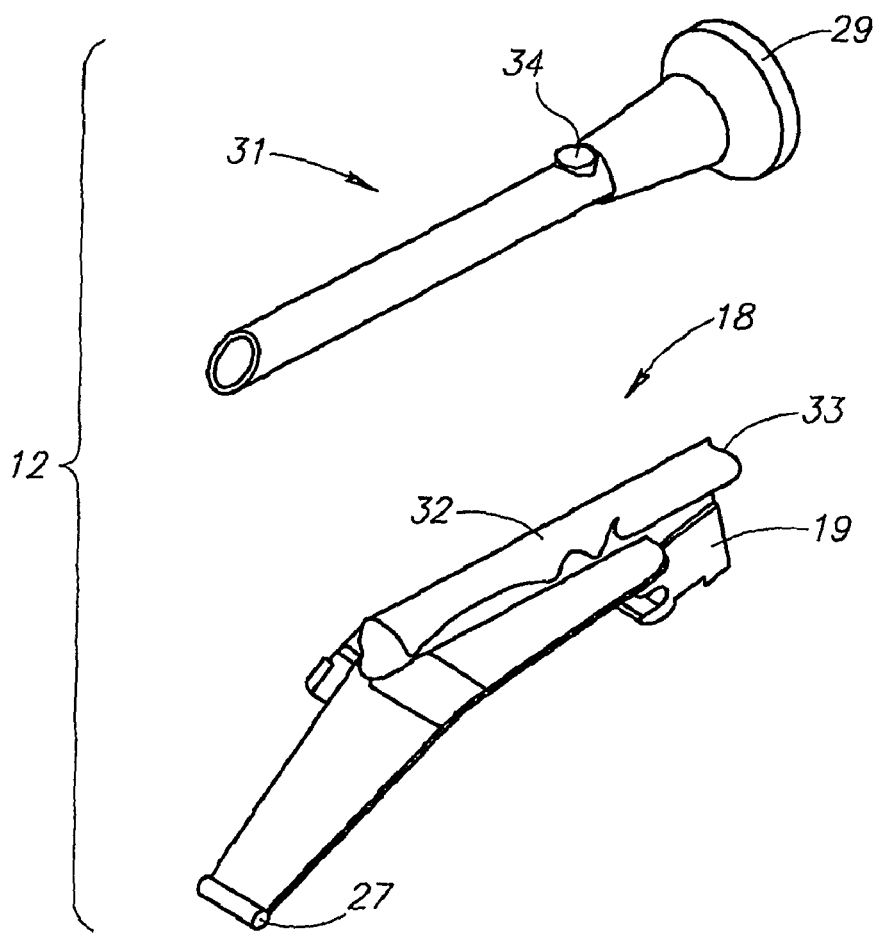
FIG. 2 is an exploded view of laryngoscope apparatus with a discrete optical view tube.
Figure 3:
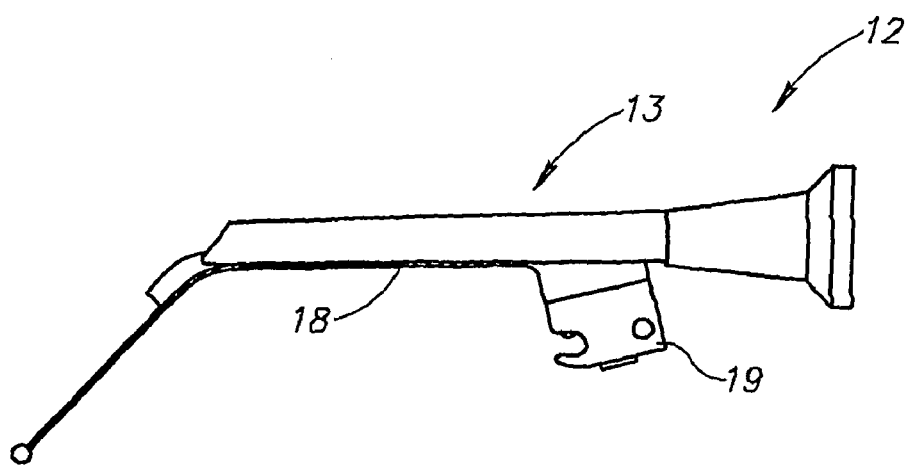
FIG. 3 is a side view of laryngoscope apparatus including an integral optical system.

FIGS. 1 to 3 show a laryngoscope 10 including a laryngoscope handle 11 and laryngoscope apparatus 12 including an optical system 13 having a straight optical axis 14 corresponding to a non-deflected Line Of Sight (LOS) and affording a Field Of View (FOV) 16 along a deflected LOS 17 in a median plane through the midline of a human body for assisting an intubation procedure. The FOV 16 has a most deflected LOS ray 17A relative to the optical axis 14 and a minor axis A and a major axis B in the median plane resulting in a distortion value A/B. The laryngoscope apparatus 12 includes a curved laryngoscope blade 18 with a base 19 for double snap fitting onto the laryngoscope handle 11 into an operative intubation position in a conventional manner. The laryngoscope blade 18 has a spatula 21 with a tongue engaging surface 22 and a teeth engaging surface 23. The laryngoscope blade 18 includes a trailing spatula section 24 and a leading spatula section 26 terminating in a leading blade tip 27.

The laryngoscope apparatus 12 includes an optical view tube 28 having an eyepiece 29 and housing the optical system 13. The optical view tube 28 is coextensive with the trailing spatula section 24 and demarcates the leading spatula section 26 extending therebeyond. The laryngoscope apparatus 12 can be a two part system including a discrete optical view tube 31 for use with a laryngoscope blade 18 formed with an elongated holder 32 for slidingly receiving the optical view tube 31 (see FIG. 2). The holder 32 has a recess 33 for receiving a stopper 34 formed on the optical view tube 31 for aligning the optical view tube 31 relative to the holder 32. The laryngoscope apparatus 12 can include a laryngoscope blade 18 with an integral optical system 13 (see FIG. 3).

The laryngoscope apparatus 12 is preferably designed such that FOV's most deflected LOS ray 17A coincides with the leading spatula section 26. This arrangement maximizes visual utilization of the available FOV 16 but prevents occurrence of a blind spot between the FOV 16 and the blade tip 27 which would otherwise exist if the leading spatula section 26 be deflected away from the optical axis 14 to a greater extent than the FOV's most deflected LOS ray 17A. Against this, in the case the FOV's most deflected LOS ray 17A is deflected away from the optical axis 14 more than the leading spatula section 26, the laryngoscope apparatus 12 would not be fully utilizing the available FOV 16.

The laryngoscope 10 preferably includes a conventional illumination arrangement for providing illumination light for assisting intubation and a conventional defogging arrangement for defogging the forwardmost optical surface of its optical system.

Figure 4:
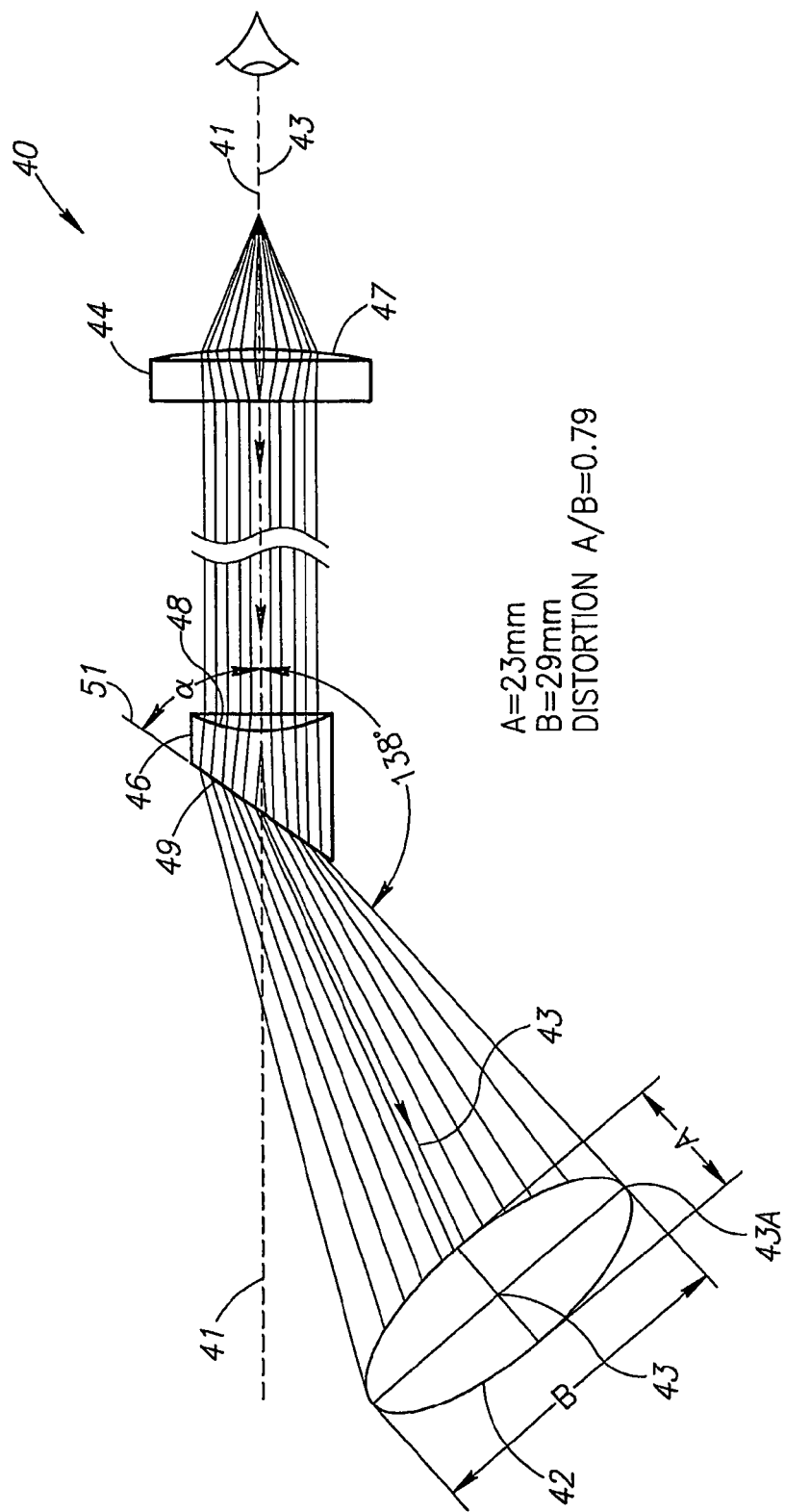
FIG. 4 is a ray diagram of a conventional optical system showing its FOV.
Figure 6:
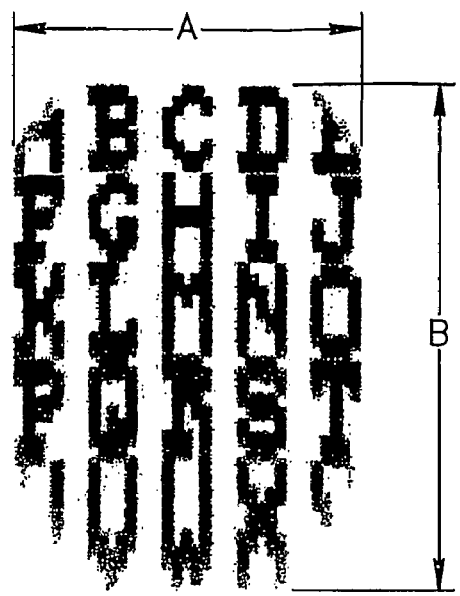
FIG. 6 is a pictorial representation of FIG. 4's FOV.
Figure 7:
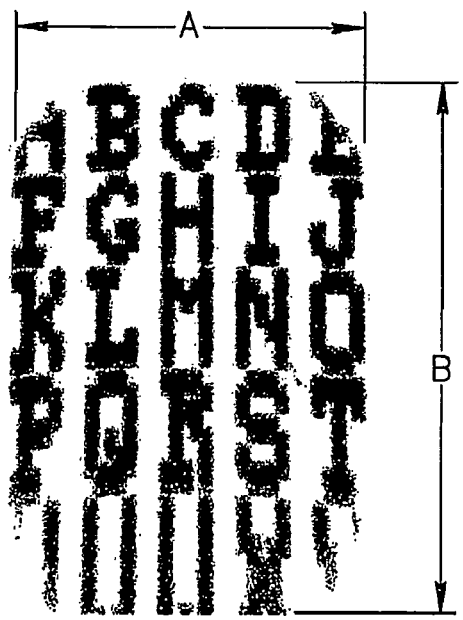
FIG. 7 is a pictorial representation of FIG. 5's FOV.

Truphatek International Ltd., Netanya, Israel, the owners of the present invention, supply laryngoscope apparatus 12 based on the Rothfels principle under the tradename Truview™ Evo-2. FIG. 4 shows a Truview™ Evo-2 optical system 40 having a straight optical axis 41 corresponding to a non-deflected LOS and affording a FOV 42 along a deflected LOS 43. The FOV 42 has a most deflected LOS ray 43A and a minor axis A=23 mm and a major axis B=29 mm resulting in a distortion value A/B=0.79 (see FIG. 6). The optical system 40 includes an eyepiece lens 44 and an aperture lens 46. The eyepiece lens 44 has a plano-convex shape with a rearmost convex surface 47. The aperture lens 46 has a rearmost concave surface 48 facing towards the eyepiece lens 44 and a forwardmost flat inclined prism surface 49 facing away therefrom. The forwardmost flat inclined prism surface 49 defines an imaginary plane 51 subtending an inclined acute prism angle $\alpha=55\pm0.5°$ with the optical axis 41. The aperture lens 46 has a Clear Aperture Diameter (CAD) of about 8.5 mm and effects a total FOV magnification defined by the major axis $B/CAD=29/8.5\approx3.4\pm0.1$. The Truview™ Evo-2 optical system 40 deflects the most deflected LOS ray 43A away from the optical axis 41 by 42° shown as the complementary angle 138°.

Figure 5:
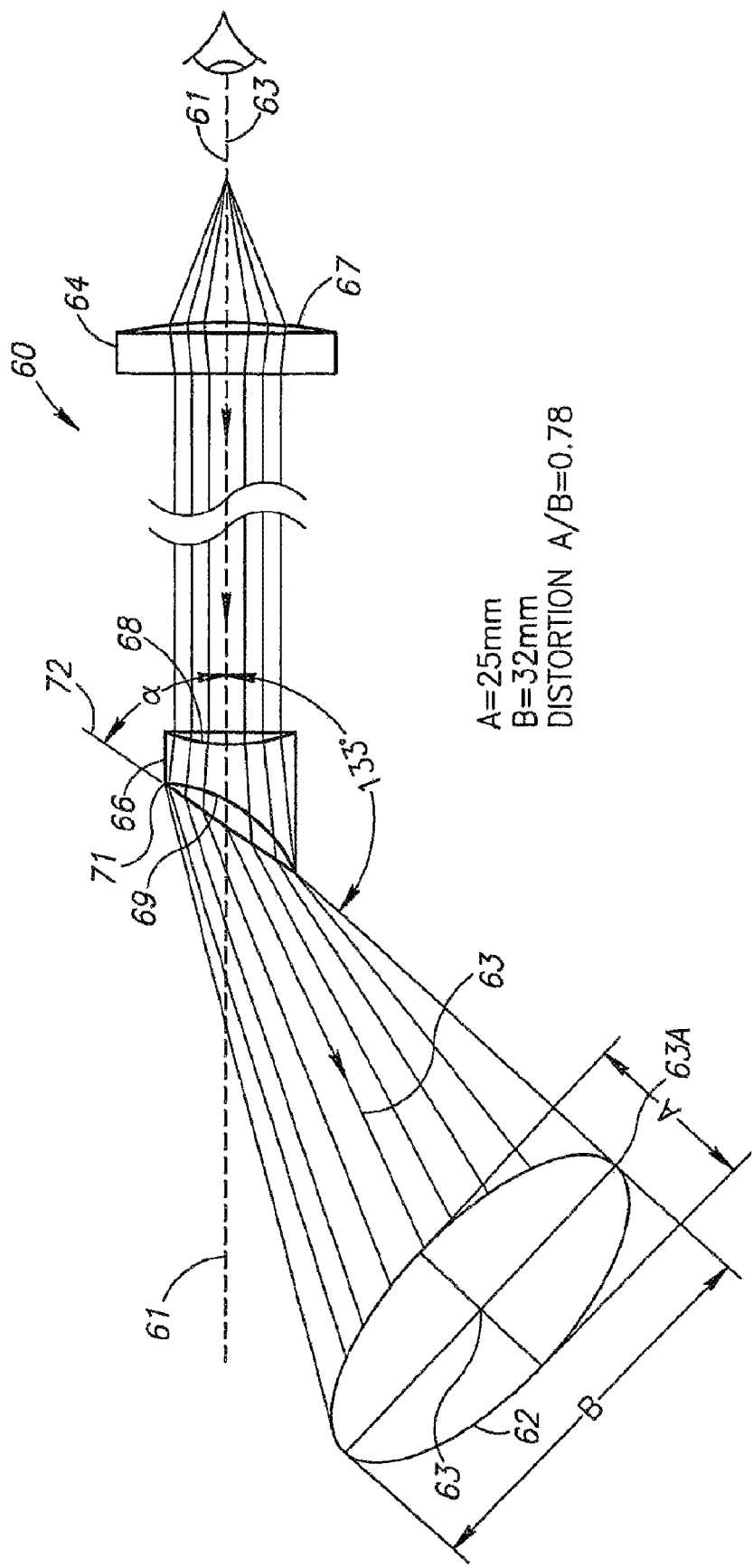
FIG. 5 is a ray diagram of an optical system of the present invention showing its FOV.

FIG. 5 shows an optical system 60 similar in construction and operation to the optical system 40. The optical system 60 has a straight optical axis 61 corresponding to a non-deflected LOS and affording a FOV 62 along a deflected LOS 63 and having a most deflected LOS ray 63A. The optical system 60 includes an eyepiece lens 64 and an aperture lens 66 with the same Clear Aperture Diameter (CAD) as the aperture lens 46. The eyepiece lens 64 includes a rearmost convex surface 67 similar to the eyepiece lens 44. The aperture lens 66 includes a rearmost concave surface 68 similar to the rearmost concave surface 48 and a forwardmost concave inclined prism surface 69. The forwardmost concave inclined prism surface 69 has an annular rim 71 which defines an imaginary plane 72 subtending the same inclined acute prism angle $\alpha=55\pm0.5°$ with the optical axis 61.

The FOV 62 has a minor axis A=25 mm and a major axis B=32 mm resulting in a distortion value A/B=0.78. The aperture lens 66 effects a total FOV magnification defined by the major axis $B/CAD=32/8.5\approx3.7\pm0.1$ and deflects the most deflected LOS ray 63A away from the optical axis 61 by 47° shown as the complementary angle 133°. The total FOV magnification of about $3.7\pm0.1$ is achieved by a major contribution by the rearmost concave surface 68 serving to provide an initial FOV magnification of about $3.4\pm0.1$ as per the aperture lens 46 whilst the forwardmost concave inclined prism surface 69 provides the remaining additional FOV magnification.

Figure 8:
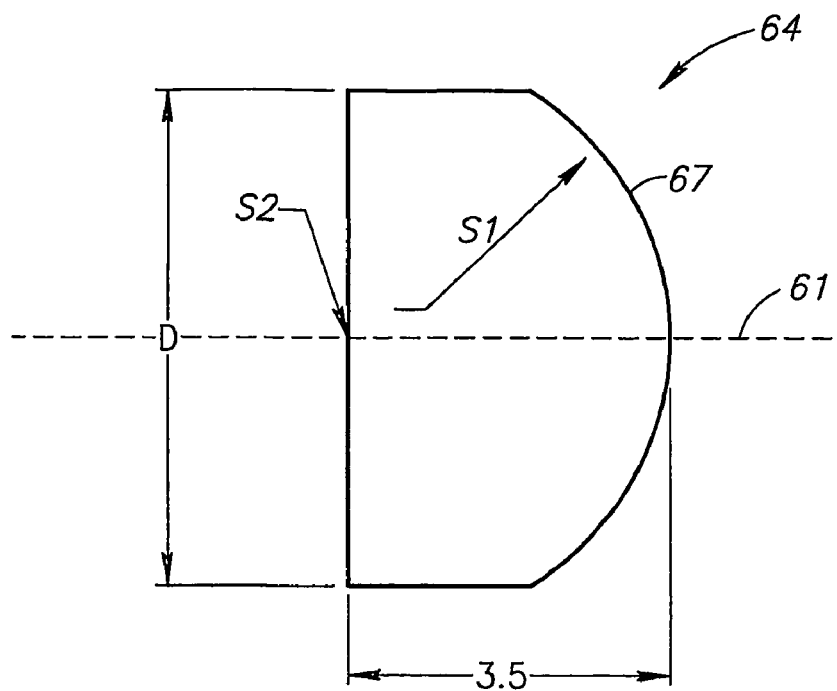
FIG. 8 is a side view of an eyepiece lens of FIG. 5's optical system.

FIG. 8 shows the dimensions and other technical details of the eyepiece lens 64 including inter alia:

D=15 mm; Focal length+150 mm

Surface 67: Radius Of Curvature (ROC) $77.52\pm0.2$ mm

Figure 9:
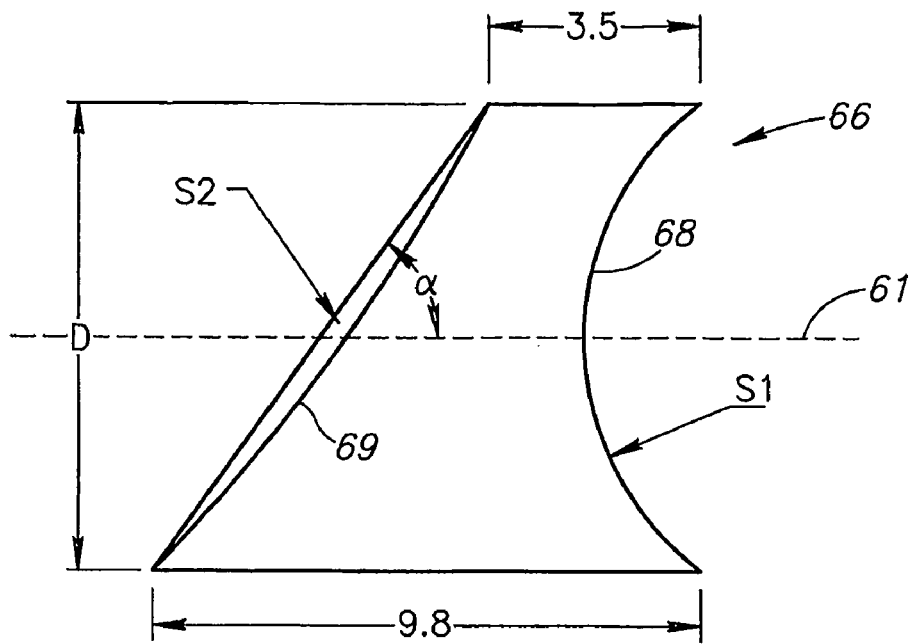
FIG. 9 is a side view of an aperture lens of FIG. 5's optical system.

FIG. 9 shows the dimensions and other technical details of the aperture lens 66 including inter alia:

D=9 mm; Focal length −37.63 mm

Surface 68: ROC $22.06\pm0.1$ mm

Surface 69: ROC $180.0\pm3.0$ mm

Comparison Between Optical Systems 40 and 60

The optical system 60 provides a total FOV magnification B/CAD of about $32/8.5\approx3.7\pm0.1$ compared to the optical system 40's total FOV magnification $29/8.53\approx4\pm0.1$ thereby affording a 47° most deflected LOS ray 63A in comparison to the 42° most deflected LOS ray 43A. This additional LOS deflection enables a more curved laryngoscope blade coinciding with the most deflected LOS ray 63A which enables less patient manipulation and/or application of force to achieve the same visualization. The FOV 62 also has a 25 mm minor axis A which is wider than the FOV 42's 23 mm minor axis A which further assists in correct ETT placement. The optical system 60 marginally increases the optical system 40's distortion value A/B 0.79 to 0.78.

While the invention has been described with respect to a limited number of embodiments, it will be appreciated that many variations, modifications, and other applications of the invention can be made within the scope of the appended claims.

The invention claimed is:

1. Laryngoscope apparatus comprising:
   (a) a curved laryngoscope blade having a trailing spatula section and a leading spatula section terminating at a leading blade tip; and
   (b) an optical system having a line of sight with a field of view and including an eyepiece lens and an aperture lens defining an optical axis,
   said aperture lens located along said laryngoscope blade for demarcating said leading spatula section,
   said aperture lens having a rearmost concave surface and a forwardmost concave inclined prism surface respectively facing towards and away from said eyepiece lens,
   said rearmost concave surface providing an initial magnified field of view along said line of sight,
   said forwardmost concave inclined prism surface further magnifying said initial magnified field of view along said line of sight,
   said forwardmost concave inclined prism surface defining an imaginary plane subtending an included acute prism angle with said optical axis in a side view of said laryngoscope blade for deflecting said line of sight away from said optical axis beyond said aperture lens towards said blade tip, wherein said plane subtends an included prism angle $\alpha=55°\pm3.0°$ and said forwardmost concave inclined prism surface has an $180\pm6.0$ mm radius of curvature.

2. Apparatus according to claim 1 wherein said rearmost concave surface provides an initial field of view magnification of about $3.4\pm0.1$ of a total field of view magnification of said aperture lens of about $3.7\pm0.1$.

3. Apparatus according to claim 1 wherein said plane subtends an included prism angle $\alpha=55°\pm0.5°$ and said forwardmost concave inclined prism surface has an $180\pm3.0$ mm radius of curvature.

4. The laryngoscope apparatus according to claim 1 and further including a laryngoscope handle, said laryngoscope blade permanently, pivotally mounted on the laryngoscope handle so as to be pivotal between an inoperative storage position and an operative intubation position.

5. The laryngoscope apparatus according to claim 1 wherein said the leading spatula section of the blade extends at an angle to the trailing spatula section that coincides with the angle between the most deflected line of sight ray and the optical axis.

6. The optical view tube according to claim 5 wherein said angle between the trailing spatula section and the leading spatula section of the blade is about 47 degrees.

7. The laryngoscope apparatus according to claim 1 wherein said aperture lens is one piece.

8. An optical view tube for use in laryngoscope apparatus that includes a curved laryngoscope blade, said optical view tube being mountable on said blade and comprising
   an optical system located in said optical view tube and having a line of sight with a field of view and including an eyepiece lens and an aperture lens defining an optical axis,
   said aperture lens having a rearmost concave surface and a forwardmost concave inclined prism surface respectively facing towards and away from said eyepiece lens,
   said rearmost concave surface providing an initial magnified field of view along said line of sight,
   said forwardmost concave inclined prism surface further magnifying said initial magnified field of view along said line of sight, and defining an imaginary plane subtending an included acute prism angle with said optical axis in a side view of said laryngoscope blade for deflecting said line of sight away from said optical axis beyond said aperture lens towards said blade tip, wherein said plane subtends an included prism angle $\alpha=55°\pm3.0°$ and said forwardmost concave inclined prism surface has an $180\pm6.0$ mm radius of curvature.

9. The optical view tube according to claim 8 wherein said rearmost concave surface provides an initial field of view magnification of about $3.4\pm0.1$ of a total field of view magnification of said aperture lens of about $3.7\pm0.1$.

10. The optical view tube according to claim 8 wherein said plane subtends an included prism angle $\alpha=55°\pm0.5°$ and said forwardmost concave inclined prism surface has an $180\pm3.0$ mm radius of curvature.

11. A laryngoscope blade having a trailing spatula section and a leading spatula section terminating at a leading blade tip adapted for use in a laryngoscope apparatus comprising
   a tube holder integrally mounted to said blade;
   an optical view tube fixedly held by said tube holder;
   an optical system in said view tube, said optical system having a line of sight with a field of view and including an eyepiece lens and an aperture lens defining an optical axis,
   said aperture lens located along said laryngoscope blade for demarcating said leading spatula section,
   said aperture lens having a rearmost concave surface and a forwardmost concave inclined prism surface respectively facing towards and away from said eyepiece lens,
   said rearmost concave surface providing an initial magnified field of view along said line of sight,
   said forwardmost concave inclined prism surface further magnifying said initial magnified field of view along said line of sight,
   said forwardmost concave inclined prism surface defining an imaginary plane subtending an included acute prism angle with said optical axis in a side view of said laryngoscope blade for deflecting said line of sight away from said optical axis beyond said aperture lens towards said blade tip, wherein said plane subtends an included prism angle $\alpha=55°\pm3.0°$ and said forwardmost concave inclined prism surface has an $180\pm6.0$ mm radius of curvature.

12. The laryngoscope blade according to claim 11 wherein said the leading spatula section of the blade extends at an angle to the trailing spatula section that coincides with the angle between the most deflected line of sight ray and the optical axis.

13. The laryngoscope blade according to claim 12 wherein said angle between the trailing spatula section and the leading spatula section of the blade is about 47 degrees.

14. The laryngoscope blade according to claim 11 wherein said rearmost concave surface provides an initial field of view magnification of about $3.4\pm0.1$ of a total field of view magnification of said aperture lens of about $3.7\pm0.1$.

15. The laryngoscope blade according to claim 11 wherein said plane subtends an included prism angle $\alpha=55°\pm0.5°$ and said forwardmost concave inclined prism surface has an $180\pm3.0$ mm radius of curvature.

16. In a laryngoscope apparatus comprising a curved laryngoscope blade having a trailing spatula section and a leading spatula section terminating at a leading blade tip, and
   an optical system having a line of sight with a field of view and including an eyepiece lens and an aperture lens defining an optical axis, said aperture lens located along said laryngoscope blade for demarcating said leading spatula section, said aperture lens having a rearmost concave surface and a forwardmost inclined prism surface respectively facing towards and away from said eyepiece lens, said rearmost concave surface providing an initial magnified field of view along said line of sight, said forwardmost inclined prism surface defining an imaginary plane subtending an included acute prism angle with said optical axis in a side view of said laryngoscope blade for deflecting said line of sight away from said optical axis beyond said aperture lens towards said blade tip;

the improvement comprising:

said forwardmost inclined prism surface of said aperture lens being concave so as to increase the deflection of said line of sight away from said optical axis beyond said aperture lens towards said blade tip, and to further magnify said initial magnified field of view along said line of sight, wherein said plane subtends an included prism angle $\alpha=55°\pm3.0°$ and said forwardmost concave inclined prism surface has an $180\pm6.0$ mm radius of curvature.

* * * * *